(12) United States Patent
Kubo et al.

(10) Patent No.: US 10,159,416 B2
(45) Date of Patent: Dec. 25, 2018

(54) BIOLOGICAL INFORMATION MEASURING APPARATUS AND BIOLOGICAL INFORMATION MEASURING METHOD

(71) Applicant: NIHON KOHDEN CORPORATION, Tokyo (JP)

(72) Inventors: Hiroshi Kubo, Tokyo (JP); Yukio Koyama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 309 days.

(21) Appl. No.: 14/799,678

(22) Filed: Jul. 15, 2015

(65) Prior Publication Data

US 2016/0029903 A1    Feb. 4, 2016

(30) Foreign Application Priority Data

Jul. 30, 2014    (JP) .................................. 2014-155481

(51) Int. Cl.
*A61B 5/0215* (2006.01)
*A61B 5/0402* (2006.01)
(Continued)

(52) U.S. Cl.
CPC ........ *A61B 5/0215* (2013.01); *A61B 5/02116* (2013.01); *A61B 5/0402* (2013.01);
(Continued)

(58) Field of Classification Search
CPC . A61B 5/0215; A61B 5/02116; A61B 5/0402; A61B 5/0456; A61B 5/7278;
(Continued)

(56) References Cited

U.S. PATENT DOCUMENTS 5,169,379 A * 12/1992 Freed .................... A61M 1/106
                                                              600/17
5,365,933 A    11/1994 Elghazzawi
(Continued)

FOREIGN PATENT DOCUMENTS

JP    3-030774 A    2/1991
JP    3-202069 A    9/1991
(Continued)

OTHER PUBLICATIONS

El-Ghazzawi, et al.; "An Algorithm to Extract Blood-Pressure Waveform Features During Intra-Aortic Balloon Pump Assist", Anesthesia Technology, Nov. 1989, 2 pages total.
(Continued)

*Primary Examiner* — Navin Natnithithadha
(74) *Attorney, Agent, or Firm* — Sughrue Mion, PLLC

(57) ABSTRACT

A biological information measuring apparatus and a biological information measuring method are provided. The biological information measuring apparatus includes a pulsation information detecting unit configured to detect heartbeat information relating to a heartbeat of a subject, a blood pressure waveform measuring unit configured to measure a blood pressure waveform of the subject in an invasive manner, and a calculating unit configured to detect a cardiac cycle from the heartbeat information and to calculate, based on a detection of a maximal blood pressure value of the blood pressure waveform in the cardiac cycle, at least one of a systolic pressure of the subject, an end-diastolic pressure of the subject, an augmentation pressure of an IABP (intra-aortic balloon pumping), a systolic pressure assisted by the IABP and an end-diastolic pressure assisted by the IABP.

21 Claims, 8 Drawing Sheets

(51) Int. Cl.
*A61B 5/0456* (2006.01)
*A61B 5/021* (2006.01)
*A61B 5/00* (2006.01)
*A61M 1/10* (2006.01)
*A61M 1/12* (2006.01)

(52) U.S. Cl.
CPC .......... *A61B 5/0456* (2013.01); *A61B 5/7278* (2013.01); *A61B 5/4851* (2013.01); *A61M 1/106* (2013.01); *A61M 1/1072* (2013.01); *A61M 1/1086* (2013.01); *A61M 1/125* (2014.02); *A61M 2230/04* (2013.01); *A61M 2230/30* (2013.01)

(58) Field of Classification Search
CPC ..... A61B 5/4851; A61M 1/125; A61M 1/106; A61M 1/1072; A61M 1/1086; A61M 2230/04; A61M 2230/30
USPC .................. 600/481, 483, 485, 486, 490–503
See application file for complete search history.

(56) References Cited

U.S. PATENT DOCUMENTS

| | | | | |
|---|---|---|---|---|
| 5,392,780 A | * | 2/1995 | Ogino | A61B 5/021 600/483 |
| 6,082,105 A | * | 7/2000 | Miyata | A61M 1/1072 60/410 |
| 6,290,641 B1 | * | 9/2001 | Nigroni | A61M 1/1086 600/18 |
| 6,679,829 B2 | * | 1/2004 | Nigroni | A61M 1/1086 600/18 |
| 2001/0034469 A1 | * | 10/2001 | Nigroni | A61M 1/1086 600/18 |
| 2005/0148812 A1 | | 7/2005 | Nigroni et al. | |

FOREIGN PATENT DOCUMENTS

| | | |
|---|---|---|
| JP | 5-161612 A | 6/1993 |
| JP | 10-127587 A | 5/1998 |
| JP | 2007503883 A | 3/2007 |
| JP | 2012-213474 A | 11/2012 |

OTHER PUBLICATIONS

Search Report dated Dec. 4, 2015, issued by the European Patent Office in counterpart European Application No. 15176563.3.
Communication dated Feb. 28, 2017, issued by the Japanese Patent Office in counterpart Japanese application No. 2014-155481.
Office Action dated Sep. 27, 2017 by the Japanese Patent Office in counterpart Japanese Patent Application No. 2014-155481.

* cited by examiner

BIOLOGICAL INFORMATION MEASURING APPARATUS AND BIOLOGICAL INFORMATION MEASURING METHOD

CROSS-REFERENCE TO RELATED APPLICATION(S)

The present application claims priority from Japanese Patent Application No. 2014-155481 filed on Jul. 30, 2014, the entire content of which is incorporated herein by reference.

BACKGROUND

The presently disclosed subject matter relates to a biological information measuring apparatus and a biological information measuring method for measuring a blood pressure.

An intra-aortic balloon pumping (IABP) is a circulation assisting apparatus which is widely used for a left ventricle. In an IABP, a balloon catheter is placed in the thoracic descending aorta of a subject, and the balloon is inflated and deflated in synchronization with the pulsation of the heart to pressure-assist the heart to increase oxygen supply to the cardiac muscle and to reduce oxygen consumption by the cardiac muscle.

For example, JP2007-503883A discloses an apparatus having a function of optimally setting the treatment timing of an IABP.

In some cases, during use of an IABP, invasive blood pressure is measured by using a biological information monitor. A biological information monitor measures the maximum, minimum, and average values of the blood pressure for each cardiac cycle, and displays the values on a biological information monitor. However, the blood pressure values displayed on the monitor during use of the IABP are most likely balloon-assisted blood pressure values.

When evaluating effects of the IABP treatment or deciding whether to wean from the IABP, it is important to know the blood pressure originating from the heart of the subject (in other words, the blood pressure value not assisted by the IABP). However, as described above, the biological information monitor may display balloon-assisted blood pressure values. Therefore, doctors or the like may not be able to correctly evaluate effects of the IABP treatment or decide whether to wean from the IABP. Moreover, doctors or the like may not be able to correctly determine the degree of assistance by the IABP. That is, doctors or the like may not be able to obtain accurate blood pressure values during use of the IABP.

SUMMARY

Illustrative aspects of the present invention provide a biological information measuring apparatus and a biological information measuring method according to which blood pressure values of a subject can be obtained accurately even during use of an IABP.

According to an illustrative aspect of the present invention, a biological information measuring apparatus includes a pulsation information detecting unit configured to detect heartbeat information relating to a heartbeat of a subject, a blood pressure waveform measuring unit configured to measure a blood pressure waveform of the subject in an invasive manner, and a calculating unit configured to detect a cardiac cycle from the heartbeat information and to calculate, based on a detection of a maximal blood pressure value of the blood pressure waveform in the cardiac cycle, at least one of a systolic pressure of the subject, an end-diastolic pressure of the subject, an augmentation pressure of an IABP, a systolic pressure assisted by the IABP and an end-diastolic pressure assisted by the IABP.

According to another illustrative aspect of the present invention, a biological information measuring method includes detecting heartbeat information relating to a heartbeat of a subject, measuring a blood pressure waveform of the subject in an invasive manner, detecting a cardiac cycle of a heart from the heartbeat information, and calculating at least one of a systolic pressure of the subject, an end-diastolic pressure of the subject, an augmentation pressure of an IABP, a systolic pressure assisted by the IABP, and an end-diastolic pressure assisted by the IABP, based on a detection of a maximal blood pressure value of the blood pressure waveform in the cardiac cycle.

According to another illustrative aspect of the present invention, a non-transitory computer readable medium stores a program that, when executed by a computer, causes the computer to execute a method including receiving heartbeat information relating to a heartbeat of a subject, and a blood pressure waveform of the subject measured in an invasive manner, detecting a cardiac cycle of a heart from the heartbeat information, and calculating at least one of a systolic pressure of the subject, an end-diastolic pressure of the subject, an augmentation pressure of an IABP, a systolic pressure assisted by the IABP, and an end-diastolic pressure assisted by the IABP, based on a detection of a maximal blood pressure value of the blood pressure waveform in the cardiac cycle.

According to another illustrative aspect of the present invention, a program causes the computer to execute a method including receiving heartbeat information relating to a heartbeat of a subject, and a blood pressure waveform of the subject measured in an invasive manner, detecting a cardiac cycle of a heart from the heartbeat information, and calculating at least one of a systolic pressure of the subject, an end-diastolic pressure of the subject, an augmentation pressure of an IABP, a systolic pressure assisted by the IABP, and an end-diastolic pressure assisted by the IABP, based on a detection of a maximal blood pressure value of the blood pressure waveform in the cardiac cycle.

DETAILED DESCRIPTION

Figure 1:
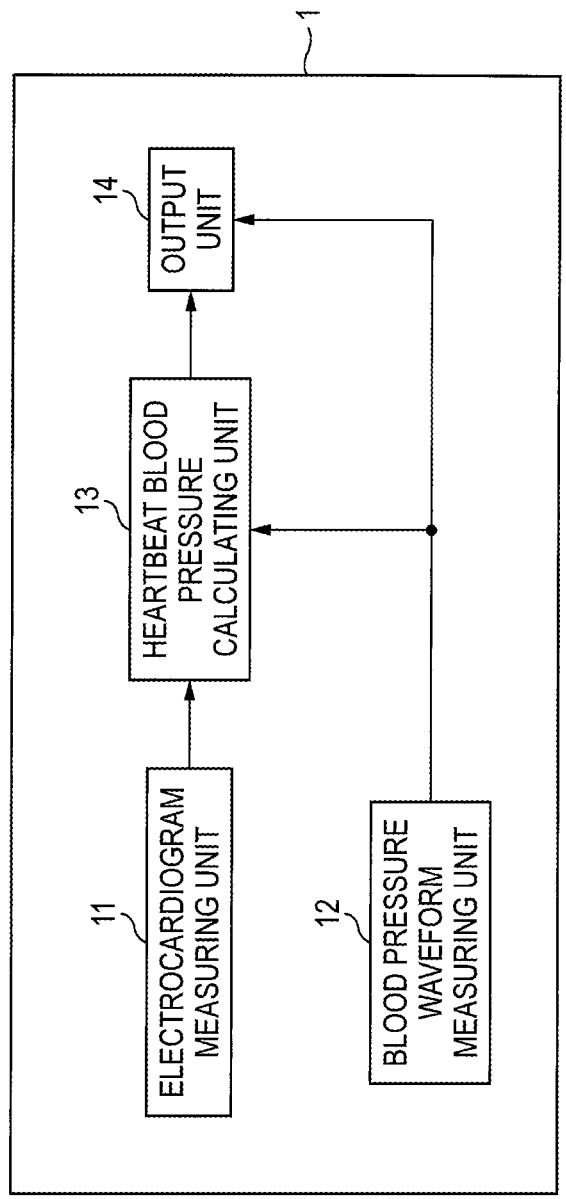
FIG. 1 is a block diagram illustrating a configuration of a biological information measuring apparatus according to an exemplary embodiment of the present invention.

Hereinafter, an exemplary embodiment of the present invention will be described with reference to the drawings. FIG. 1 is a block diagram showing a configuration of a biological information measuring apparatus 1 according to an exemplary embodiment of the present invention. The biological information measuring apparatus 1 has an electrocardiogram measuring unit 11, a blood pressure waveform measuring unit 12, a heartbeat blood pressure calculating unit 13, and an output unit 14. The biological information measuring apparatus 1 is configured to invasively measure the blood pressure. Examples of the biological information measuring apparatus 1 includes a biological information monitor and an invasive manometer. In the following description, it is assumed that an intra-aortic balloon pumping (IABP) is used in the subject to be measured by the biological information measuring apparatus 1.

The electrocardiogram measuring unit 11 has, for example, electrocardiogram electrodes and an amplifying circuit. The electrocardiogram electrodes are attached to the chest and the like of the subject. The electrocardiogram measuring unit 11 acquires an ECG (Electrocardiogram) based on electrocardiogram signals obtained from the electrocardiogram electrodes, and supplies the acquired ECG to the heartbeat blood pressure calculating unit 13.

The blood pressure waveform measuring unit 12 invasively measures the blood pressure waveform of the subject. The blood pressure waveform measuring unit 12 includes, for example, a blood pressure transducer, an amplifying circuit, a catheter, various tubes and a three-way cock. The user such as a doctor adjusts the zero point of the blood pressure value before start of the measurement of the blood pressure.

When the arterial blood pressure is to be measured, the doctor or the like inserts a catheter (arterial needle) into the radial artery of the subject. In the case where the venous blood pressure is measured, a Swan-Ganz catheter may be used. In the blood pressure waveform measuring unit 12, the blood pressure transducer converts the blood pressure to a blood pressure signal, and a blood pressure waveform which is obtained from the blood pressure signal is supplied to the heartbeat blood pressure calculating unit 13 and the output unit 14. The process of measuring the blood pressure waveform may be performed by the blood pressure waveform measuring unit 12, in a similar manner as a usual invasive blood pressure measurement process (see, e.g., Sakurai and Watanabe, "M E Hayawakari Q&A 3-Ketsuatsukei, Shinpakushutsuryokei, Ketsuryukei", NANKODO, pp. 33-92).

The ECG and the blood pressure waveform are input to the heartbeat blood pressure calculating unit 13. The heartbeat blood pressure calculating unit 13 calculates values of the blood pressure which is not assisted by the IABP (values of the blood pressure due to the heartbeat of the subject) in addition to values of the blood pressure assisted by a balloon. The method of calculation will be described in detail.

Figure 2:
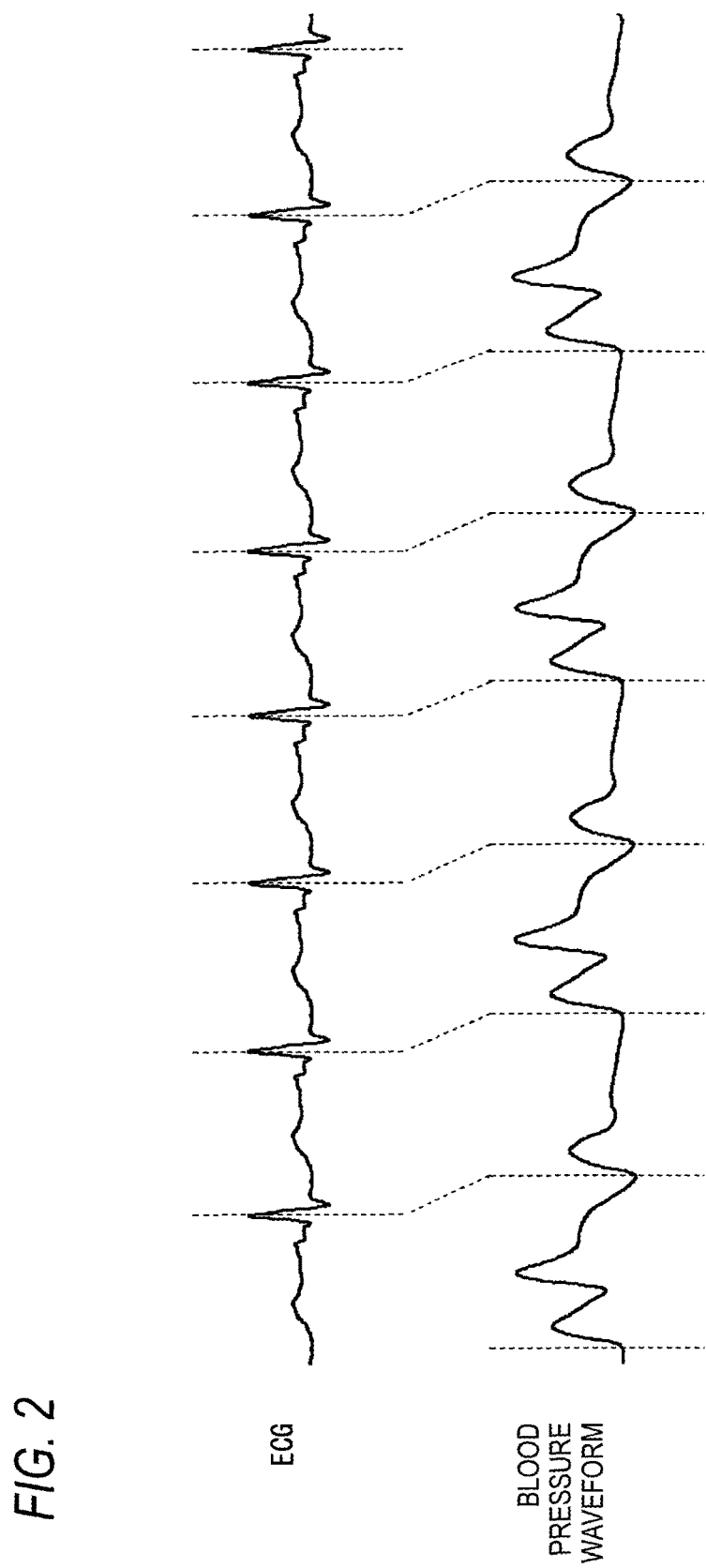
FIG. 2 is a view showing an ECG and blood pressure waveform that are input to a heartbeat blood pressure calculating unit of the biological information measuring apparatus.
Figure 3:
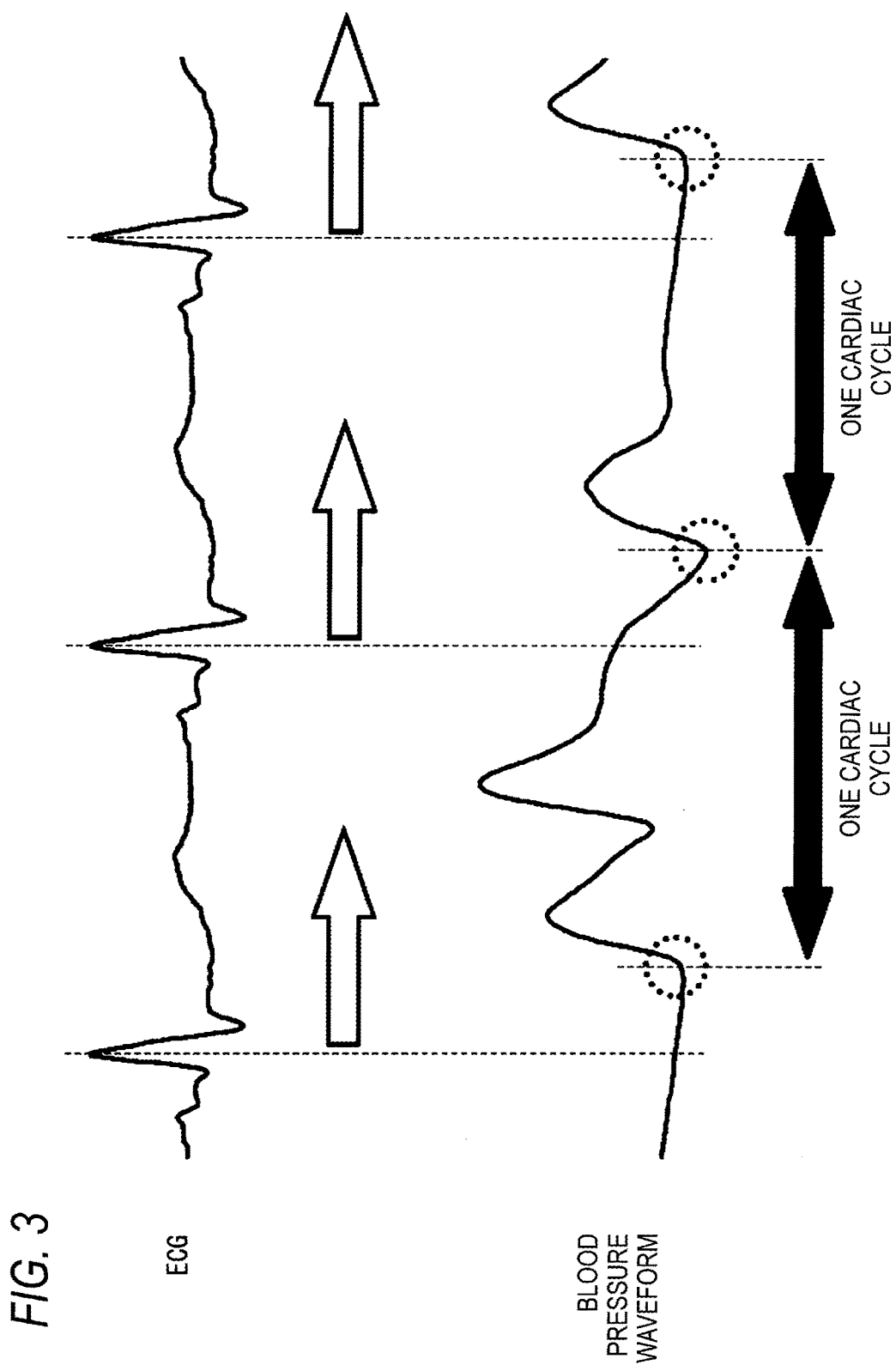
FIG. 3 is a diagram illustrating a concept of detection of a cardiac cycle by the heartbeat blood pressure calculating unit.

FIGS. 2 and 3 are views showing the ECG and blood pressure waveform which are input to the heartbeat blood pressure calculating unit 13. In the ECG, as illustrated, a QRS wave exists in each beat. The so-called R-R interval corresponds to a cardiac cycle (one heartbeat period). In treatment using an IABP, the balloon is deflated during the systolic phase of the heart of the subject, and, during the diastolic phase, the balloon is inflated at the same time when the aortic valve closes. Usually, the balloon of an IABP is inflated and deflated in synchronization with the blood pressure (blood pressure waveform) or an ECG. Therefore, the peak point of the blood pressure waveform in a predetermined time period after the detection of a QRS wave can be deemed as a point of beginning the systolic phase (the portion enclosed by a dotted circle in FIG. 3). The peak point is a point where the blood pressure value transitions from descent to ascent. When exceeding the peak point, the blood pressure value is sharply increased.

The heartbeat blood pressure calculating unit 13 analyzes the ECG to detect a QRS wave. The heartbeat blood pressure calculating unit 13 detects above-described peak points in the predetermined time period from the QRS wave. The heartbeat blood pressure calculating unit 13 treats the interval of the detected peak points as a cardiac cycle. FIG. 3 is a view showing the concept of detection of the cardiac cycle by the heartbeat blood pressure calculating unit 13. In the example of FIG. 3, the IABP performs a so-called 1:2 assist (during two cardiac cycles, a balloon assist is performed in one of the cardiac cycles). Here, the heartbeat blood pressure calculating unit 13 detects a peak value on the descending side of the blood pressure which is in the predetermined time period from the detection of a QRS wave. Since a peak value on the descending side of the blood pressure is used (instead of a peak value on the side where the blood pressure is high), the heartbeat blood pressure calculating unit 13 can accurately detect a cardiac cycle irrespective of the operation timing of the IABP.

Figure 4:
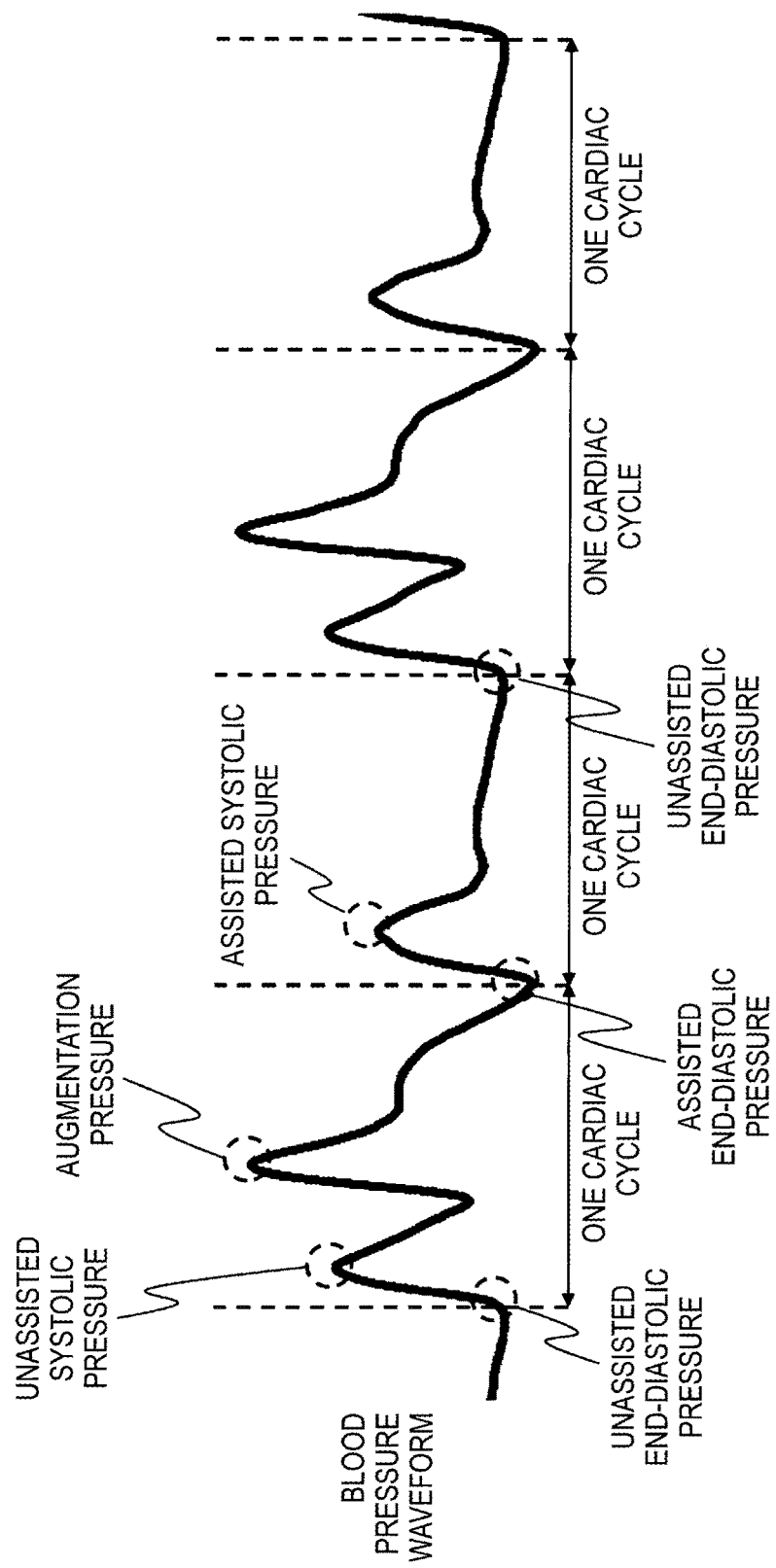
FIG. 4 is a conceptual diagram illustrating a method of calculating pressure values by the heartbeat blood pressure calculating unit.

FIG. 4 is a conceptual diagram showing a method of calculating pressure values by the heartbeat blood pressure calculating unit 13. In the example of FIG. 4, cardiac cycles with two maximal values, and cardiac cycles with one maximal value alternately appear (the assist ratio is 1:2).

The heartbeat blood pressure calculating unit 13 detects a maximal value of the blood pressure in each detected cardiac cycle. A maximal value is a peak point where the blood pressure transitions from ascent to descent. Except in cases of arrhythmia, dicrotic wave, and the like, in the case of a cardiac cycle in which balloon assist is not performed, one maximal value appears in one cardiac cycle. In the case of a cardiac cycle in which balloon assist is performed, two maximal values appear in one cardiac cycle. The heartbeat blood pressure calculating unit 13 does not treat peak points (so-called noises or dicrotic wave) where ascent and descent of the blood pressure value are repeated in a short time period (predetermined time period), as a maximal value. The heartbeat blood pressure calculating unit 13 may perform a filtering process as preprocessing in order to eliminate the influence of noises and the like. The heartbeat blood pressure calculating unit 13 estimates the IABP assist ratio in accordance with situation of detection of a maximal value (the detection number of a maximal value in one cardiac cycle). With respect to the blood pressure waveform of FIG. 4, for example, the heartbeat blood pressure calculating unit 13 presumes that the assist ratio is 1:2.

In the case where the mode of the IABP is presumed to be 1:n (n being two or more), the heartbeat blood pressure calculating unit 13 detects the first maximal value in one cardiac cycle where two maximal values appear, as the subject's own systolic pressure (see FIG. 4). The heartbeat blood pressure calculating unit 13 further detects the second maximal value in one cardiac cycle where two maximal values appear, as the augmentation pressure (the value of the pressure assisted by the IABP) (see FIG. 4). The heartbeat blood pressure calculating unit 13 detects a peak point (point where the blood pressure value transitions from descent to ascent) which appears immediately before the unassisted systolic pressure of the subject, as the unassisted end-diastolic pressure of the subject (see FIG. 4). The method of detecting the unassisted end-diastolic pressure is not limited to this. For example, the heartbeat blood pressure calculating unit 13 may detect the minimum value of the blood pressure in a time period which is a predetermined time period earlier than the detected unassisted systolic pressure of the subject, as the unassisted end-diastolic pressure of the subject (FIG. 4). Furthermore, the heartbeat blood pressure calculating unit 13 detects a peak point (point where the blood pressure value transitions from descent to ascent) which appears immediately after the augmentation pressure, as the end-diastolic pressure assisted by the IABP (see FIG. 4). The heartbeat blood pressure calculating unit 13 may detect the minimum value of the blood pressure in a time period which is a predetermined time period after the timing of detecting the augmentation pressure, as the assisted end-diastolic pressure (see FIG. 4). Furthermore, the heartbeat blood pressure calculating unit 13 detects a maximal value which appears solely in one cardiac cycle, as the systolic pressure assisted by the IABP.

Figure 5:
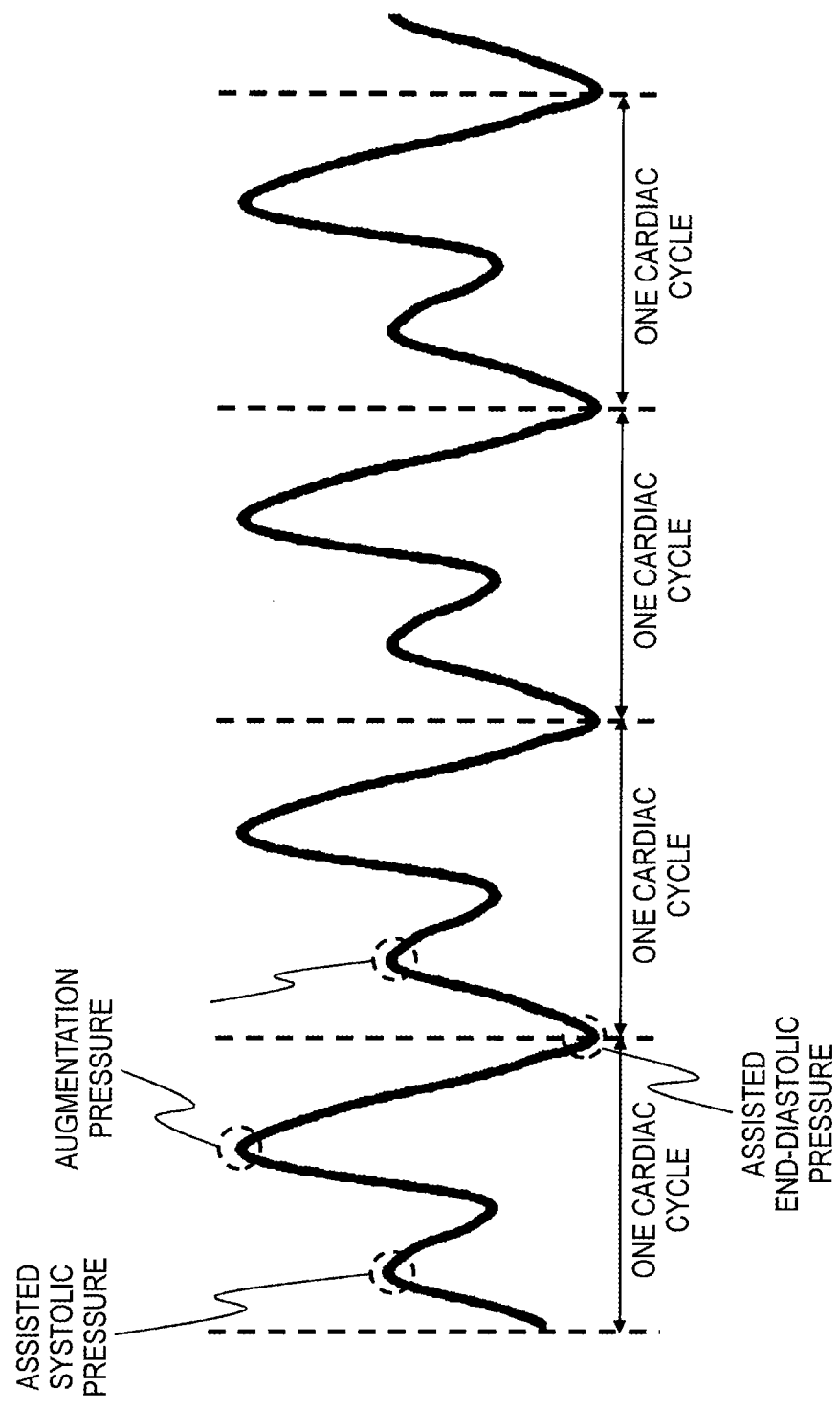
FIG. 5 is a conceptual diagram illustrating another method of calculating pressure values by the heartbeat blood pressure calculating unit.

The method of calculating the blood pressure value in the case where the IABP assist ratio is 1:1 will be described with reference to FIG. 5. When the mode of the IABP is 1:1, the heartbeat blood pressure calculating unit 13 detects the first maximal value in each cardiac cycle, as the assisted systolic pressure (see FIG. 5). The heartbeat blood pressure calculating unit 13 detects the second maximal value in each cardiac cycle, as the augmentation pressure (see FIG. 5). The heartbeat blood pressure calculating unit 13 detects a peak point (point where the blood pressure value transitions from descent to ascent) which appears immediately before the assisted systolic pressure, as the end-diastolic pressure assisted by the IABP (see FIG. 5). This is performed because, in the case where the mode of the IABP is 1:1, the heartbeat assist by the balloon is always performed in each cardiac cycle. In the case where the IABP assist ratio is 1:1, the heartbeat blood pressure calculating unit 13 may detect the minimum value of the blood pressure in each cardiac cycle as the assisted end-diastolic pressure. Moreover, the heartbeat blood pressure calculating unit 13 may detect the minimum value of the blood pressure in a time period which is a predetermined time period before the timing of detecting the assisted systolic pressure, as the assisted end-diastolic pressure.

Furthermore, the heartbeat blood pressure calculating unit 13 may further calculate the time period between the unassisted systolic pressure and the augmentation pressure. In this case, the heartbeat blood pressure calculating unit 13 determines whether the difference between the calculated time period (time period between the unassisted systolic pressure and the augmentation pressure) and a predetermined time period is within a given range or not. The predetermined time period is a preferable time period (when high effects of treatment are achieved) from the unassisted systolic pressure in the IABP treatment to the augmentation pressure. If the difference is not within the given range, therefore, the heartbeat blood pressure calculating unit 13 determines that the treatment timing of the IABP (operation timing of the balloon) is not adequate. In the case where the biological information measuring apparatus 1 measures also the arterial pressure (ART), the heartbeat blood pressure calculating unit 13 may perform a comparison with waveform of the ART, and determine whether the operation timing of the IABP is adequate or not.

A user of the biological information measuring apparatus 1 (e.g., a doctor) may input mode information explicitly indicating whether the IABP is being used or not. The user may input the mode information by operating an input unit (not shown) of the biological information measuring apparatus 1. The input unit may be, for example, a button or a touch display provided on a housing of the biological information measuring apparatus 1. The mode information may contain information of the assist ratio. In the case where a ratio of 1:3 is input as the assist ratio, when the heartbeat blood pressure calculating unit 13 detects two maximal values in certain one cardiac cycle, for example, the unit is controlled so as to detect only one maximal value in subsequent two cardiac cycles. As described above, the assist ratio is explicitly known, and therefore the heartbeat blood pressure calculating unit 13 can more adequately calculate pressure values. In the case where the assist ratio is explicitly input, the heartbeat blood pressure calculating unit 13 may calculate pressure values by using the assist ratio. When the assist ratio is designated as 1:1, for example, the heartbeat blood pressure calculating unit 13 may determine the minimum blood pressure value of each cardiac cycle, as the assisted end-diastolic pressure.

Depending on the characteristics of the subject, influences of noise, and the like, the blood pressure value may repeatedly perform fine ascent and descent operations. Therefore, the heartbeat blood pressure calculating unit 13 is controlled so as not to treat a peak value (point where the blood pressure transitions from ascent to descent) which may be caused by fine ascent and descent operations, as a maximal value. Even in the case where the IABP is used, it is adequate that the unit is controlled while assuming that three or more maximal values do not appear in one cardiac cycle. In other words, when the heartbeat blood pressure calculating unit 13 detects three or more maximal values in one cardiac cycle, the accuracy of detecting pressure values is lowered. Therefore, the heartbeat blood pressure calculating unit 13 detects only an adequate peak value as a maximal value.

The output unit 14 outputs the blood pressure waveform and the blood pressure values calculated by the heartbeat blood pressure calculating unit 13. The output unit 14 displays the blood pressure waveform acquired by the blood pressure waveform measuring unit 12, in the form of a time-series graph, and also the pressure values calculated by the heartbeat blood pressure calculating unit 13. Hereinafter, examples of the output of the output unit 14 will be described.

Figure 6:
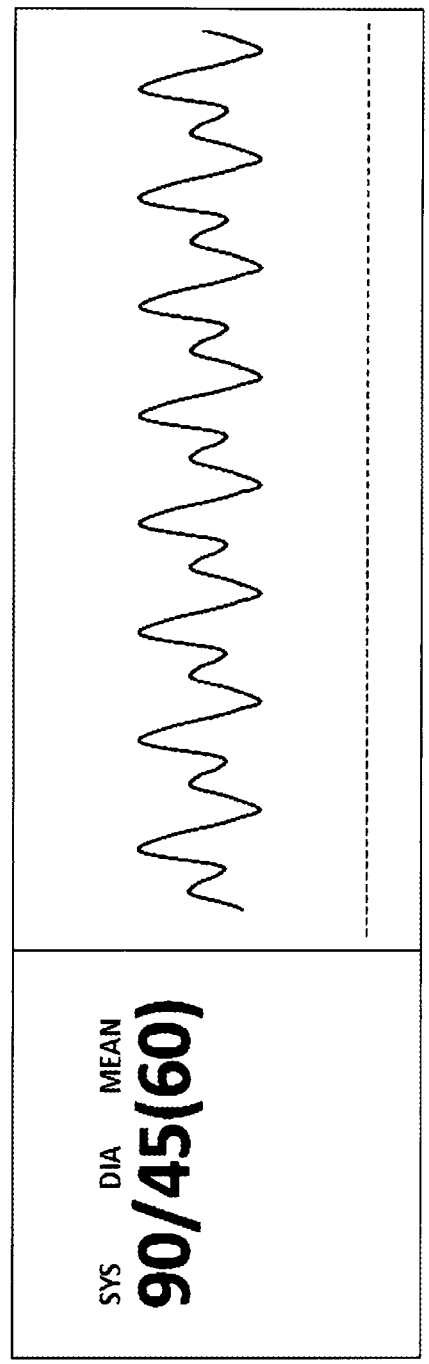
FIG. 6 is a view illustrating an example of an output screen produced by an output unit of the biological information measuring apparatus.

In a first example, the output unit 14 displays the systolic pressure and end-diastolic pressure which are designated by the user, as numerical values on a display screen. Here, the designation means whether the values are blood pressure values of the subject, or those of the blood pressure assisted by the balloon. FIG. 6 shows an example of the display screen. The display screen is similar to a blood pressure display screen of a usual biological information monitor, but the displayed blood pressure values are the systolic pressure and diastolic pressure which are selected by the user. When the user designates that the systolic pressure and end-diastolic pressure of the subject are to be displayed, for example, the output unit 14 displays the systolic pressure and end-diastolic pressure of the subject, as numerical values.

Figure 7A:
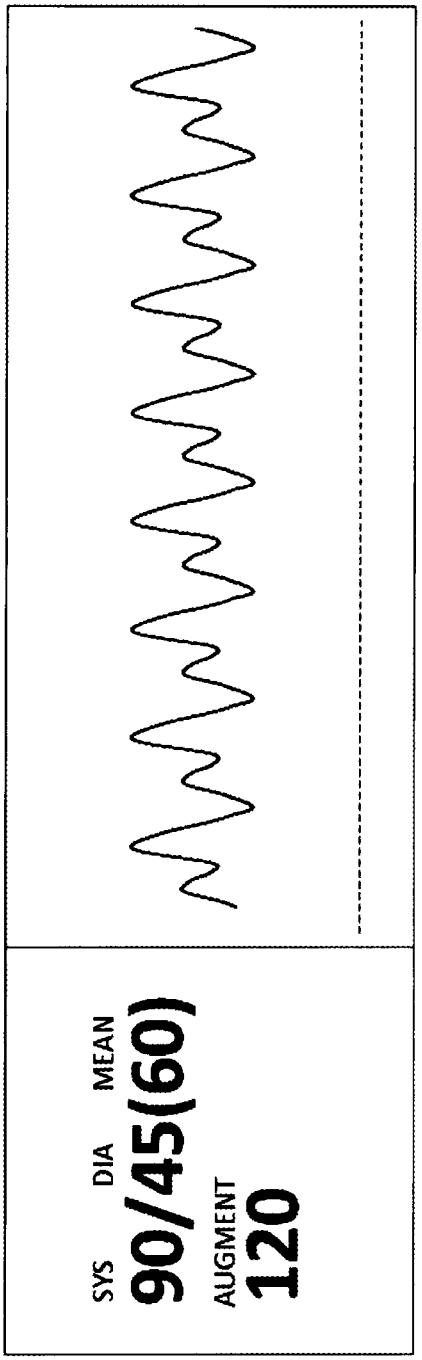
FIGS. 7A and 7B are views illustrating examples of the output screen produced by the output unit.
Figure 7B:
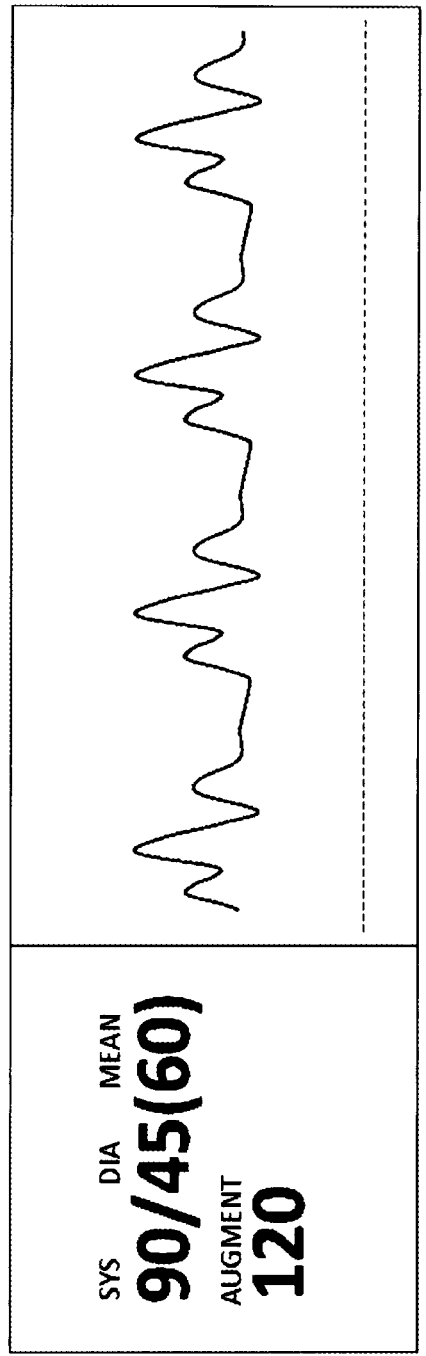

A second example will be described with reference to FIGS. 7A and 7B. The output unit 14 may simultaneously display the systolic pressure of the subject and the augmentation pressure. FIG. 7A is a view showing the display screen in the case where the assist ratio is 1:1, and FIG. 7B is a view showing the display screen in the case where the assist ratio is 1:2. As illustrated, the augmentation pressure (AUGMENT) and the systolic pressure (SYS) of the subject are separately displayed. When referring to the display screen, the doctor or the like can know the systolic pressure of the subject distinctly from the augmentation pressure.

Figure 8:
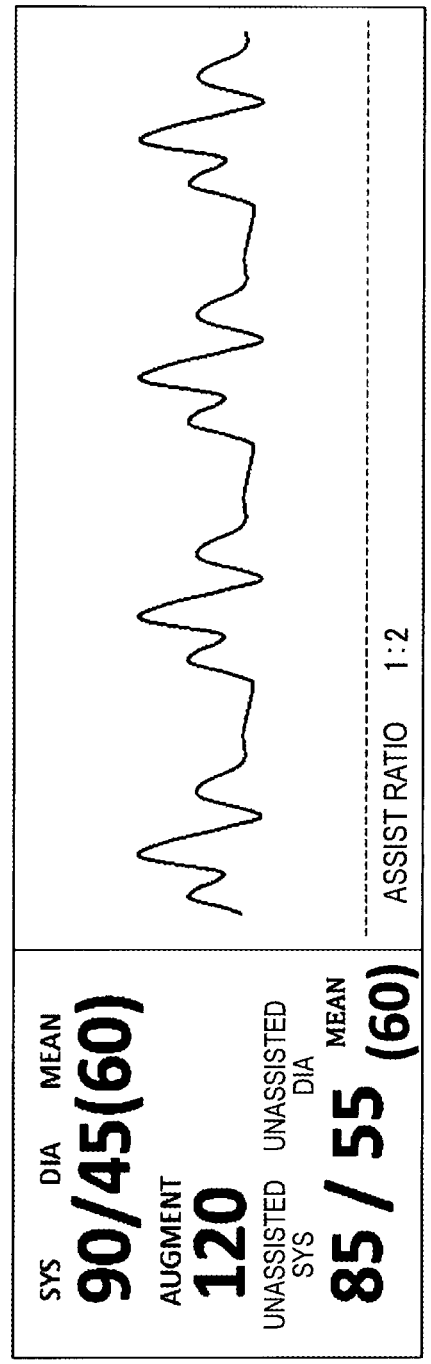
FIG. 8 is another view illustrating an example of the output screen produced by the output unit.

A third example will be described with reference to FIG. 8. the output unit 14 displays all the pressure values calculated by the heartbeat blood pressure calculating unit 13 (i.e., the systolic pressure of the subject, the augmentation pressure, the end-diastolic pressure of the subject, the end-diastolic pressure assisted by the IABP, and the systolic pressure assisted by the IABP), and the assist ratio on a same display screen. As shown in FIG. 8, all pressure values detected by the heartbeat blood pressure calculating unit 13 are displayed on the display screen. When seeing the display screen, the doctor or the like can know the effects of the IABP, the stated of the heartbeat (the states of blood pressure values) of the subject, and the like.

The output unit 14 may display also the time period from the systolic pressure of the subject to the augmentation pressure. As described above, when the time period is inadequate (too short or too long), it is possible to determine that the treatment timing of the IABP (operation timing of the balloon) is not adequate. If the heartbeat blood pressure calculating unit 13 determines that the treatment timing of the IABP (operation timing of the balloon) is not adequate, the output unit 14 may output a display or sound attracting the user's attention. This enables the doctor or the like to change the setting of the IABP so as to perform proper treatment.

Next, effects of the biological information measuring apparatus 1 according to the exemplary embodiment will be described. During the balloon operation of the IABP, two maximal blood pressure values exist in one cardiac cycle. When the balloon of the IABP is not operated, one maximal value of the blood pressure exists in one cardiac cycle. As described above, the biological information measuring apparatus 1 calculates a cardiac cycle, and, in accordance with the detection of the maximal blood pressure value in one cardiac cycle, further calculates the systolic pressure of the subject, the augmentation pressure (blood pressure assisted by the IABP), and the end-diastolic pressure of the subject. When referring the end-diastolic pressure of the subject which is displayed distinctly from the augmentation pressure, the doctor or the like can easily determine effects of the IABP treatment or weaning from the IABP.

Usually, the balloon of an IABP is inflated and deflated in synchronization with the blood pressure (blood pressure waveform) or an ECG. In the R wave of an ECG, moreover, the voltage is largely changed. Based on the timing of detecting the QRS wave of the ECG, the heartbeat blood pressure calculating unit 13 can accurately calculate the blood pressure values of the subject (the systolic pressure and the end-diastolic pressure), and values of blood pressures assisted by the IABP (the systolic pressure and the end-diastolic pressure).

The output unit 14 displays the calculated systolic pressure and end-diastolic pressure of the subject, together with the blood pressure waveform on the display screen (FIGS. 6 to 8). Therefore, the doctor or the like can visually recognize the systolic pressure and end-diastolic pressure of the subject during use of the IABP. Since the systolic pressure and end-diastolic pressure of the subject can be recognized, the doctor or the like can clearly know the appropriateness of weaning from the IABP, and effects of the IABP treatment.

Preferably, the heartbeat blood pressure calculating unit 13 calculates the blood pressure values by using the mode information (information indicating whether the IABP is used or not, and the assist ratio) which is explicitly designated. By having the assist ratio in advance, the heartbeat blood pressure calculating unit 13 can determine timings when two maximal values appear in one cardiac cycle. Therefore, the likelihood of erroneous detection by the heartbeat blood pressure calculating unit 13 can be remarkably reduced.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

In the above-described example, a cardiac cycle is calculated by using the ECG. The invention is not limited to this. The ECG is used for obtaining information (heartbeat information) relating to the pulsation (heartbeat) of the heart. Therefore, a configuration other than the electrocardiogram measuring unit 11 may be employed in so far as it can obtain heartbeat information relating to the heartbeat of the subject. For example, the pulse wave may be detected by using an SpO2, and the cardiac cycle may be estimated from the pulse wave to perform the process described above. That is, the biological information measuring apparatus 1 has a pulsation information detecting unit configured to obtain heartbeat information of the subject (an ECG in the example of FIG. 1). The electrocardiogram measuring unit 11 is a mode of the pulsation information detecting unit.

In a related art, the measurement of blood pressure values during use of an IABP has not been deeply studied. Accordingly, the biological information measuring apparatus 1 is advantageous even it is configured to calculate only at least one of the systolic pressure and end-diastolic pressure of the subject in the manner described above. That is, the biological information measuring apparatus 1 may be configured to calculate and to output a necessary blood pressure value in accordance with designation (e.g., designation using a button) by the doctor or the like. In other words, the biological information measuring apparatus 1 may be configured to calculate at least one of the systolic pressure of the subject, the end-diastolic pressure of the subject, the augmentation pressure of the IABP, the systolic pressure assisted by the IABP, and the end-diastolic pressure assisted by the IABP. For example, the biological information measuring apparatus 1 may be configured to detect only the second maximal value in one cardiac cycle to detect only the augmentation pressure.

The processes in the heartbeat blood pressure calculating unit 13 and the output unit 14 may be implemented by computer programs which operate in the biological information measuring apparatus 1. That is, the biological information measuring apparatus 1 includes also a configuration which has a usual computer, such as a central processing unit (CPU) and a memory device.

The programs may be stored in a non-transitory computer readable medium of any one of various types, and then supplied to the computer. The non-transitory computer readable medium includes tangible storage media of various types. Examples of the non-transitory computer readable medium are a magnetic recording medium (e.g., a flexible disk, a magnetic tape, and a hard disk drive), a magneto-optical recording medium (e.g., a magneto-optical disk), a CD-read only memory (CD-ROM), a CD-R, a CD-R/W, a semiconductor memory (e.g., a mask ROM, a programmable ROM (PROM), an erasable PROM (EPROM), a flash ROM, and a random access memory (RAM)). Alternatively, the programs may be supplied to the computer by means of a transitory computer readable medium of any one of various types. Examples of the transitory computer readable medium are an electrical signal, an optical signal, and an electromagnetic wave. The transitory computer readable medium can supply the programs to the computer through a wired communication path such as a metal wire or an optical fiber, or a wireless communication path.

What is claimed is:

1. A biological information measuring apparatus comprising:
    a pulsation information detecting unit configured to detect heartbeat information relating to a heartbeat of a subject;
    a blood pressure waveform measuring unit configured to measure a blood pressure waveform of the subject in an invasive manner;
    a processor configured to detect a cardiac cycle in the blood pressure waveform by using the heartbeat information, to determine or receive an intra-aortic balloon pumping assist ratio, and to determine, based on the intra-aortic balloon pumping assist ratio and a detection of a maximal blood pressure value of the blood pressure waveform in the cardiac cycle, at least one of:
        a systolic pressure of the subject,
        an end diastolic pressure of the subject,
        an augmentation pressure produced by an external intra-aortic balloon pumping, a systolic pressure produced with assistance by the intra-aortic balloon pumping, and
        an end-diastolic pressure produced with assistance by the intra-aortic balloon pumping; and
    a display configured to display at least one of the systolic pressure of the subject, the end diastolic pressure of the subject, the augmentation pressure produced by an external intra-aortic balloon pumping, the systolic pressure produced with assistance by the intra-aortic balloon pumping, and the end-diastolic pressure produced with assistance by the intra-aortic balloon pumping.

2. The biological information measuring apparatus according to claim 1, wherein the heartbeat information is an electrocardiogram, and
    wherein the processor is configured to detect a QRS wave from the electrocardiogram and to calculate blood pressure values with reference to a detection point of the QRS wave.

3. The biological information measuring apparatus according to claim 2, wherein the processor is configured to calculate, in a case where two maximal blood pressure values exist in the detected cardiac cycle, one of the maximal blood pressure values that appears first as the systolic pressure of the subject and the other maximal blood pressure value that appears second as the augmentation pressure of the intra-aortic balloon pumping.

4. The biological information measuring apparatus according to claim 1, wherein the display is further configured to display at least one of the systolic pressure of the subject and the end-diastolic pressure of the subject, together with the blood pressure waveform in a form of a time-series graph.

5. The biological information measuring apparatus according to claim 1, further comprising an input unit through which mode information is input, the mode information indicating whether the intra-aortic balloon pumping is being used on the subject, and
    wherein the processor detects the maximal blood pressure value of the blood pressure waveform based on the mode information.

6. The biological information measuring apparatus according to claim 1, wherein, in a case where two maximal blood pressure values exist in the detected one cardiac cycle, the processor determines whether an operation timing of the intra-aortic balloon pumping is normal, based on a time interval between the two maximal blood pressure values.

7. The biological information measuring apparatus according to claim 1, wherein the processor is configured to determine, based on the intra-aortic balloon pumping assist ratio and a detection of a maximal blood pressure value of the blood pressure waveform in the cardiac cycle, at least one of:
    the augmentation pressure produced by an external intra-aortic balloon pumping,
    the systolic pressure produced with assistance by the intra-aortic balloon pumping, and
    the end-diastolic pressure produced with assistance by the intra-aortic balloon pumping.

8. The biological information measuring apparatus according to claim 1, wherein the processor detects a plurality of cardiac cycles and determines the intra-aortic balloon pumping assist ratio by detecting a number of maximal values of blood pressure in each detected cardiac cycle among the plurality of cardiac cycles.

9. The biological information measuring apparatus according to claim 1, further comprising an input interface, wherein the input interface is configured to receive user input indicating the intra-aortic balloon pumping assist ratio.

10. The biological information measuring apparatus according to claim 1, wherein the intra-aortic balloon pumping assist ratio is indicative of a single intra-aortic balloon pumping assist being performed every N cardiac cycles, wherein N is a natural number.

11. The biological information measuring apparatus according to claim 1, wherein the processor is further configured to, based on the intra-aortic balloon pumping assist ratio and a detection of a maximal blood pressure value of the blood pressure waveform in a plurality of detected cardiac cycles, determine at least one of:
    the systolic pressure of the subject,
    the end diastolic pressure of the subject,
    the augmentation pressure produced by an external intra-aortic balloon pumping,
    the systolic pressure produced with assistance by the intra-aortic balloon pumping, and
    the end-diastolic pressure produced with assistance by the intra-aortic balloon pumping.

12. A biological information measuring method comprising:
    detecting heartbeat information relating to a heartbeat of a subject;
    measuring a blood pressure waveform of the subject in an invasive manner;
    detecting a cardiac cycle of in the blood pressure waveform by using the heartbeat information;
    determining or receiving, with a processor, an intra-aortic balloon pumping assist ratio;
    determining, with the processor, based on the intra-aortic balloon pumping assist ratio and a detection of a maximal blood pressure value of the blood pressure waveform in the cardiac cycle, at least one of:
        a systolic pressure of the subject, an end-diastolic pressure of the subject,
an augmentation pressure produced by an external intra-aortic balloon pumping,
a systolic pressure produced with assistance by the intra-aortic balloon pumping, and
an end-diastolic pressure produced with assistance by the intra-aortic balloon pumping; and displaying, on a display, at least one of the systolic pressure of the subject, the end-diastolic pressure of the subject, the augmentation pressure produced by an external intra-aortic balloon pumping, the systolic pressure produced with assistance by the intra-aortic balloon pumping, and the end-diastolic pressure produced with assistance by the intra-aortic balloon pumping.

13. The biological information measuring method according to claim 12, wherein determining or receiving, with the processor, the intra-aortic balloon pumping assist ratio comprises:
detecting a plurality of cardiac cycles; and
determining, with the processor, the intra-aortic balloon pumping assist ratio by detecting a number of maximal values of blood pressure in each detected cardiac cycle among the plurality of cardiac cycles.

14. The biological information measuring method according to claim 12, wherein determining or receiving, with the processor, the intra-aortic balloon pumping assist ratio comprises:
receiving, via an input interface, user input indicating the intra-aortic balloon pumping assist ratio.

15. The biological information measuring method according to claim 12, wherein the intra-aortic balloon pumping assist ratio is indicative of a single intra-aortic balloon pumping assist being performed every N cardiac cycles, wherein N is a natural number.

16. The biological information measuring method according to claim 12, further comprising determining, with the processor, based on the intra-aortic balloon pumping assist ratio and a detection of a maximal blood pressure value of the blood pressure waveform in a plurality of detected cardiac cycles, at least one of:
the systolic pressure of the subject,
the end-diastolic pressure of the subject,
the augmentation pressure produced by an external intra-aortic balloon pumping,
the systolic pressure produced with assistance by the intra-aortic balloon pumping, and
the end-diastolic pressure produced with assistance by the intra-aortic balloon pumping.

17. A non-transitory computer readable medium storing a program that, when executed by a computer, causes the computer to execute a method comprising:
receiving heartbeat information relating to a heartbeat of a subject, and a blood pressure waveform of the subject measured in an invasive manner;
detecting a cardiac cycle in the blood pressure waveform by using the heartbeat information;
determining or receiving, with a processor, an intra-aortic balloon pumping assist ratio; and
determining, with the processor, based on the intra-aortic balloon pumping assist ratio and a detection of a maximal blood pressure value of the blood pressure waveform in the cardiac cycle, at least one of:
a systolic pressure of the subject,
an end-diastolic pressure of the subject,
an augmentation pressure produced by an external intra-aortic balloon pumping,
a systolic pressure produced with assistance by the intra-aortic balloon pumping,
an end-diastolic pressure produced with assistance by the intra-aortic balloon pumping; and
causing a display to display at least one of the systolic pressure of the subject, the end-diastolic pressure of the subject, the augmentation pressure produced by an external intra-aortic balloon pumping, the systolic pressure produced with assistance by the intra-aortic balloon pumping, and the end-diastolic pressure produced with assistance by the intra-aortic balloon pumping.

18. The non-transitory computer readable medium according to claim 17, wherein determining or receiving, with the processor, the intra-aortic balloon pumping assist ratio comprises:
detecting a plurality of cardiac cycles; and
determining, with the processor, the intra-aortic balloon pumping assist ratio by detecting a number of maximal values of blood pressure in each detected cardiac cycle among the plurality of cardiac cycles.

19. The non-transitory computer readable medium according to claim 17, wherein determining or receiving, with the processor, the intra-aortic balloon pumping assist ratio comprises:
receiving, via an input interface, user input indicating the intra-aortic balloon pumping assist ratio.

20. The non-transitory computer readable medium according to claim 17, wherein the intra-aortic balloon pumping assist ratio is indicative of a single intra-aortic balloon pumping assist being performed every N cardiac cycles, wherein N is a natural number.

21. The non-transitory computer readable medium according to claim 17, further comprising determining, with the processor, based on the intra-aortic balloon pumping assist ratio and a detection of a maximal blood pressure value of the blood pressure waveform in a plurality of detected cardiac cycles, at least one of:
the systolic pressure of the subject,
the end-diastolic pressure of the subject,
the augmentation pressure produced by an external intra-aortic balloon pumping,
the systolic pressure produced with assistance by the intra-aortic balloon pumping, and
the end-diastolic pressure produced with assistance by the intra-aortic balloon pumping.

* * * * *